United States Patent
Takayasu (10) Patent No.: US 10,571,535 B2
(45) Date of Patent: Feb. 25, 2020

(54) ACOUSTIC DIAGNOSTIC SYSTEM AND METHOD FOR SUPERCONDUCTING DEVICES OPERATING IN GAS OR LIQUID

(71) Applicant: Massachusetts Institute of Technology, Cambridge, MA (US)

(72) Inventor: Makoto Takayasu, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/012,183

(22) Filed: Jun. 19, 2018

(65) Prior Publication Data

US 2018/0372818 A1  Dec. 27, 2018

Related U.S. Application Data

(60) Provisional application No. 62/604,036, filed on Jun. 21, 2017.

(51) Int. Cl.
*G01R 33/38* (2006.01)
*G01N 29/14* (2006.01)
(Continued)

(52) U.S. Cl.
CPC ....... *G01R 33/3804* (2013.01); *G01D 5/3538* (2013.01); *G01N 29/14* (2013.01);
(Continued)

(58) Field of Classification Search
CPC .. G01R 33/3804; G01R 31/00; G01D 5/3538; G01N 29/14; G01N 29/2418;
(Continued)

(56) References Cited

U.S. PATENT DOCUMENTS 3,950,606 A  4/1976 Schmidt
4,140,021 A  2/1979 Nomura et al.
(Continued)

OTHER PUBLICATIONS

International Search Report and Written Opinion dated Sep. 14, 2018 in corresponding PCT application No. PCT/US18/38263.
(Continued)

*Primary Examiner* — Suman K Nath
(74) *Attorney, Agent, or Firm* — Nields, Lemack & Frame, LLC (57) ABSTRACT

A novel system and method for detecting a quench of a superconducting conductor and detecting abnormal behavior of a superconducting conductor using acoustic sensor technology in the coolant of a superconducting cable and/or magnet is disclosed. This system and method is not only limited to use for superconductors, but also may be used for any device disposed in liquid and gas. Acoustic sensors are installed along a coolant space of a superconducting conductor and monitor coolant conditions. By monitoring acoustic changes, temperature changes or coolant flow disruption can be detected very quickly by an acoustic sensor array. By disposition of the acoustic sensor array in a coolant flow channel, the acoustic sensor system can quickly detect a local condition, such as the thermal status (temperature) of a superconducting cable and magnet with precise spatial resolution.

26 Claims, 8 Drawing Sheets

(51) Int. Cl.
*G01N 29/24* (2006.01)
*H01F 6/04* (2006.01)
*G01D 5/353* (2006.01)
*H01F 6/02* (2006.01)

(52) U.S. Cl.
CPC .......... *G01N 29/2418* (2013.01); *H01F 6/02* (2013.01); *H01F 6/04* (2013.01); *G01N 2201/088* (2013.01); *G01N 2291/106* (2013.01)

(58) Field of Classification Search
CPC ........ G01N 2201/088; G01N 2291/106; H01F 6/02; H01F 6/04
See application file for complete search history.

(56) References Cited

U.S. PATENT DOCUMENTS

| | | | |
|---|---|---|---|
| 2004/0231429 A1 | 11/2004 | Niezgorski et al. | |
| 2013/0221979 A1 | 8/2013 | Tekletsadik et al. | |
| 2013/0225414 A1* | 8/2013 | Amato | G01R 31/00 505/163 |
| 2017/0330653 A1* | 11/2017 | Lee | F25B 9/00 |

OTHER PUBLICATIONS

Chan et al., "Spatial and Temporal Resolution Requirements for Quench Detection in (RE)Ba2Cu3Ox Magnets Using Rayleigh-Scattering-Based Fiber Optic Distributed Sensing", Superconductor Science and Technology, vol. 26, pp. 1-12, 2013.

De Groot et al., "Real-Time Frequency Determination of Acoustic Emission for Different Fracture Mechanisms in Carbon/Epoxy Composites", Composites Science and Technology, vol. 55, pp. 405-412, 1995.

Ishigohka et al., "Method to Detect a Temperature Rise in Superconducting Coils with Piezoelectric Sensors", Applied Physics Letters, vol. 43, pp. 317-318, 1983.

Iwasa, "HTS Magnets: Stability; Protection; Cryogenics; Economics; Current Stability/Protection Activities at FBML", Cryogenics, vol. 43, pp. 303-316, 2003.

Nanato, "Detection of Temperature Rise in YBCO Coil by Time-Frequency Visualization of AE Signals", Physica C, vol. 469, pp. 1808-1810, 2009.

Tsukamoto et al., "Identification of Quench Origins in a Superconductor with Acoustic Emission and Voltage Measurements", Applied Physics Letters, vol. 39, pp. 172-174, 1981.

Tsukamoto et al., "Sources of Acoustic Emission in Superconducting Magnets", Journal of Applied Physics, vol. 54, pp. 997-1007, 1983.

Tsukamoto et al., "Correlation of Acoustic Emission with Normal Zone Occurrence in Epoxy-Impregnated Windings: An Application of Acoustic Emission Diagnostic Technique to Pulse Superconducting Magnets", Applied Physics Letters, vol. 44, pp. 922-924, 1984.

Yoneda et al., "Quench Detection/Protection of an HTS Coil by AE Signals", Physica C, vol. 471, pp. 1432-1435, 2011.

* cited by examiner

ACOUSTIC DIAGNOSTIC SYSTEM AND METHOD FOR SUPERCONDUCTING DEVICES OPERATING IN GAS OR LIQUID

This application claims priority of U.S. Provisional Patent Application Ser. No. 62/604,036, filed Jun. 21, 2017, the disclosure of which is incorporated herein by reference in its entirety.

This invention was made with Government support under Grant No. DE-FC02-93ER54186 awarded by the Department of Energy. The Government has certain rights in the invention.

BACKGROUND

Superconducting devices, such as superconducting magnets and superconducting power transmission cables, must be cooled below their critical operating temperature. In fact, only below this critical temperature are the electrical conductors of these devices superconductive. These devices are cooled with low temperature coolant fluid, which may be a gas or liquid, such as helium, hydrogen, neon, and nitrogen, and others.

When the superconducting material is cooled, the normal resistive state of the material becomes a superconductive state, and the electric resistivity of the material becomes very close to zero. However, during operation, the superconducting material can abruptly change its state change from superconductive to normal. This event is referred to as "quench". When a quench occurs, it is important to quickly discard the external applied electric power and safely dissipate the electromagnetic energy of the superconducting devices (magnet and/or power transmission cable) into a protection circuit. In order to do this, it is essential to detect the quench as quickly as possible, otherwise the superconducting conductor may be seriously degraded or potentially destroyed.

Recently, high temperature superconductors (HTS), such as Bismuth Strontium Calcium Copper Oxide (BSCCO) and Rare Earth Barium Copper Oxide (REBCO) conductors, have been developed and are commercially available. The devices made with those conductors are operated in a coolant, such as liquid nitrogen, liquid helium, liquid hydrogen or helium gas. HTS conductors have excellent mechanical properties with respect to axial and torsional strains, as well as high current density at high magnetic fields. The second generation (2G) REBCO HTS tapes will be very attractive for high field superconducting magnet applications, such as various industrial magnet devices for compact synchrocyclotrons, MRI, NMR, SMES, transformers, fault current limiters and generators, and accelerator magnets including dipoles, quadrupoles, and corrector magnets.

However, detecting a quench in these new high temperature superconductors, especially REBCO conductors, is very difficult. This is because the normal zone propagation velocities are very slow compared with other type of superconductors known as low-temperature-superconductor (LTS), such as NbTi and $Nb_3Sn$. Furthermore, the quench zone is confined to a very small area. For those reasons, it is difficult to detect a quench of HTS devices using conventional electric voltage methods. To quickly detect a quench for an HTS device, it is essential to implement a very sensitive quench detection method that can quickly detect the quench.

Various quench detection methods have been developed:
(1) Voltage detection of a normal zone,
(2) Hydraulic coolant pressure detection,
(3) Detection of acoustic emission (AE) due to cracking, delamination and rapid temperature changes of a quench, and
(4) Temperature detection by optical fibers.

To date, the voltage detection method using voltage taps has been most commonly used. The voltage taps must be mounted, such as by soldering, on a superconducting conductor and the electric wires are co-wound along the superconducting conductor in order to cancel undesired induced inductive voltages. The electric wires used for voltage taps complicate the fabrication of a magnet and its operation due to high induced voltage. Therefore, it is not desirable to install many voltage tap wires on a magnet. Other quench detections are still under development, and their usage is very limited at present.

Therefore, it would be beneficial if there were a system and method that could readily identify quench conditions without the drawbacks of the current technologies.

SUMMARY

The present system and method allow for the detection and diagnosis of abrupt changes of a device operating condition using an acoustic sensor array disposed in the coolant where the device is located. The purpose of the acoustic array is to identify, in real time, abrupt changes quickly and detect the location of the incident. It may be used, for example, for a quench detection of superconducting cables and magnets. This system and method is not limited to use with superconducting conductors such as magnets, power transmission cables, SMES, MRI, motors and generators, but could also be used for any electric devices disposed in liquid or gas. It can also be used for a liquid level meter. Further, this system and method is not limited to low temperature devices, but may also be used in room temperature or elevated higher temperature devices disposed in gas and/or liquid.

Characteristics of this acoustic sensor system and method include passive detection, a very simple voltage detection method, identification of the location where the event occurs, economical, and ease of use. This system and method are also advantageous because they does not require external excitation, such as laser-light and microwave, except for electric power, and there is no need to mount voltage taps on the conductor.

By identifying the location of an actuated acoustic sensor in the acoustic sensor array, the location of the abnormal event in a superconducting conductor can be identified by the acoustic sensor array. The system and method can be used to find the location of a quench of a superconducting magnet and/or a superconducting power transmission cable through use of the acoustic array system. Further, the system and method can be used to identify the location of an abnormal event in an element disposed in a fluid.

The acoustic sensor system continuously monitors with high spatial and temporal resolutions. Acoustic sensors are installed along a coolant space of a superconducting conductor and monitor the coolant condition. The acoustic sensors can electrically detect temperature change or coolant flow disruption very quickly. This technique is used to detect a quench and to identify the location of a quench of a superconducting magnet, or a superconducting power transmission cable. This method is very useful for superconducting conductor of a magnet and power transmission cable made of a cable-in-conduit-conductor (CICC), and is also especially useful for high temperature superconducting (HTS) conductors, such as REBCO and BSCCO HTS tape conductors.

Thus, according to one embodiment, a system for detecting events in a superconducting system is disclosed. The system comprises an enclosure; a coolant fluid disposed in the enclosure; a superconducting element disposed within the coolant fluid; and an acoustic sensor disposed in the coolant fluid, wherein the acoustic sensor detects an event in the superconducting system based on acoustic waves transmitted in the coolant fluid. The coolant fluid may be a liquid or a gas. The superconducting element may be a conductor or a magnet.

According to another embodiment, a system for determining a location of a thermal event in a superconducting system is disclosed. The system comprises an enclosure; a coolant fluid disposed in the enclosure; a superconducting element disposed within the coolant fluid; and an acoustic sensor array disposed in the coolant fluid, the acoustic sensor array comprising a plurality of acoustic sensors, wherein one or more of the plurality of acoustic sensors in the acoustic sensor array detects an event in the superconducting system based on acoustic waves transmitted in the coolant fluid, and a location of the event is determined based on which of the plurality of acoustic sensors detected the event. In certain embodiments, the acoustic sensor array comprises a linear array of equally spaced acoustic sensors. In some embodiments, the system also comprises a controller, wherein outputs of the acoustic sensor array are in communication with the controller. In some embodiments, the acoustic sensor has an optical fiber cable in communication with the controller. In some embodiments, each acoustic sensor as an independent output. In other embodiments, the outputs of the plurality of acoustic sensors are combined into a smaller number of wires, wherein a combination of wires are actuated if an event is detected and the combination of wires that is actuated is indicative of the acoustic sensor that detected the event. In these embodiments, the controller determines the location of the event based on which acoustic sensor detected the event. In certain embodiments, the superconducting element comprises a bundled cable with a center coolant channel, wherein the acoustic sensor array is disposed in the center coolant channel. In certain embodiments, the superconducting element comprises a multiple cabled conductor of sub-cables with a center coolant channel, wherein the acoustic sensor array is disposed in the center coolant channel. In other embodiments, the superconducting element comprises a rectangular conductor with coolant channels disposed on either side of the superconducting element, and wherein the acoustic sensor array is disposed in one of the coolant channels. The superconducting element may be a magnet or a power transmission cable.

According to another embodiment, a method of detecting a location of an abnormal event of an element disposed in a fluid is disclosed. The method comprises disposing an acoustic sensor array in the fluid, proximate the element, the acoustic sensor array comprising a plurality of acoustic sensors; detecting an acoustic wave caused by the abnormal event in the element by at least one acoustic sensor in the acoustic sensor array; determining the location of the abnormal event based on an identity of the at least one acoustic sensor that detected the acoustic wave. The fluid may be a liquid or a gas. The element may be a superconducting element and the fluid may be a coolant fluid.

BRIEF DESCRIPTION OF THE FIGURES

For a better understanding of the present disclosure, reference is made to the accompanying drawings, which are incorporated herein by reference and in which.

DETAILED DESCRIPTION OF INVENTION

A novel alternative to the most common method of detecting quench (i.e. voltage taps) is disclosed herein. The system and method detect a quench and magnet or cable temperature changes using acoustic sensors disposed in a coolant channel along a superconducting conductor. The acoustic sensors are small enough to be installed in a coolant channel, and are arranged to form an array along the coolant channel. Using a minimal number of electric wires, the acoustic sensor array detects an acoustic signal. This signal may be in communication with externally connected electronic devices, such as amplifiers, and allows for the determination of a quench location.

The condition of the coolant of a superconducting conductor or magnet is monitored continuously or periodically using acoustic sensors. An acoustic sensor can very quickly detect a change in condition, such as a temperature rise of a superconducting conductor or magnet. In addition, in general, acoustic sensors can diagnose the cooling condition of coolant of gas or liquid, which is affected by the temperature of a superconducting conductor or magnet.

As noted above, the acoustic sensors may be arranged as an array. Therefore, to determine the location of a quench, the acoustic sensor that generates the acoustic signal is identified. The acoustic sensors each generate an output voltage due to acoustic waves caused by changes in temperature and/or mechanical hydraulic conditions of the coolant in which the superconductor and acoustic sensors are immersed. When a quench occurs, the superconductor material generates heat that vaporizes the liquid coolant or causes thermal expansion of the coolant. Those events cause acoustic waves to be generated, which travel through the coolant and are detected by one or more acoustic sensors. Even smaller heat disturbances before quenching, such as nuclear heating condition of the coolant, may create small bubbles at the heating surface, such as the magnet surface, and generate acoustic waves. The acoustic wave signals are detected by acoustic sensors and indicate an abnormal condition of the device.

The present system is different from existing conventional Acoustic Emission (AE) type quench detection techniques. Conventional AE methods detect a quench by mechanical movement (cracking or conductor motion) of a superconducting magnet and do not monitor or record the coolant behavior. Conventional AE sensors are mounted on a magnet surface, and the sensors detect acoustic waves due to mechanical movement such as cracking of epoxy on a superconducting conductor caused by thermal stress when a magnet is cooled and quenches, or by stress due to an electromagnetic force when a magnet is charged. In other words, traditional systems rely on a mechanical change to the conductor, magnet or the attached epoxy. In contrast, the present system and method detects acoustic sound waves generated by temperature changes transmitted through the coolant fluid.

An acoustic sensor array allows identification of the location of temperature changes in a superconducting conductor. The acoustic sensors may be distributed in a coolant channel, making very quick detection possible. Furthermore, the acoustic sensor array can easily be electrically isolated from a superconducting conductor, avoiding problematic issues observed with other techniques (such as shorts with voltage taps). The acoustic sensor array is easily installed in a coolant channel. Even after fabrication, the acoustic sensor array can be inserted from one end of a superconducting conductor.

Figure 1A:
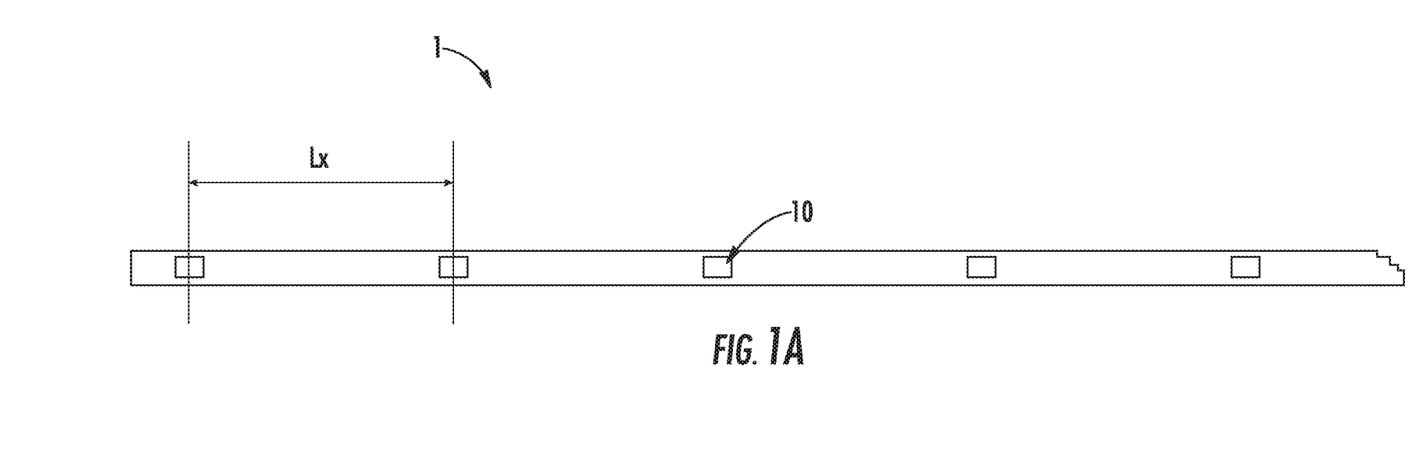
FIG. 1A shows an acoustic sensor array for use with the present system according to one embodiment and FIG. 1B shows the electrical connections for an acoustic sensor.
Figure 1B:
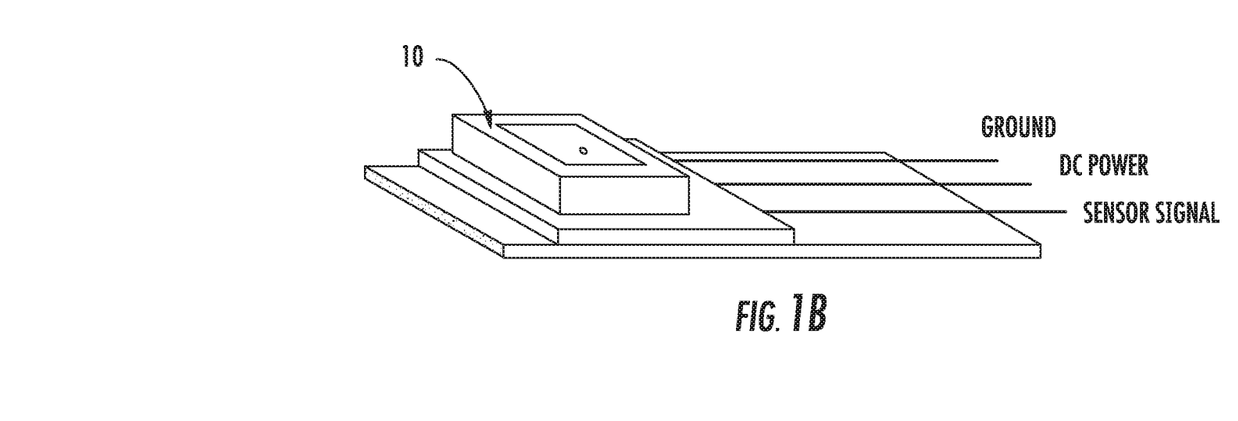

FIG. 1A shows conceptually an acoustic sensor array 1 to detect an abnormality, such as a temperature rise of a device in a coolant fluid, such as a quench of a superconducting magnet. The acoustic signals propagated in the coolant fluid are received by the sensors 10 of the acoustic sensor array 1. This acoustic sensor array 1 may be a linear array, where each of the acoustic sensors 10 is separated from the adjacent sensor by a distance Lx. Of course, in other embodiments, the acoustic sensor array may be a two dimensional array. The acoustic sensor array 1 may be comprised of micro acoustic sensors 10, also referred to as microphones (shown in FIG. 2). Each acoustic sensor 10 has three signals associated with it, as shown in FIG. 1B. These are the power, ground and output signals.

Figure 2:
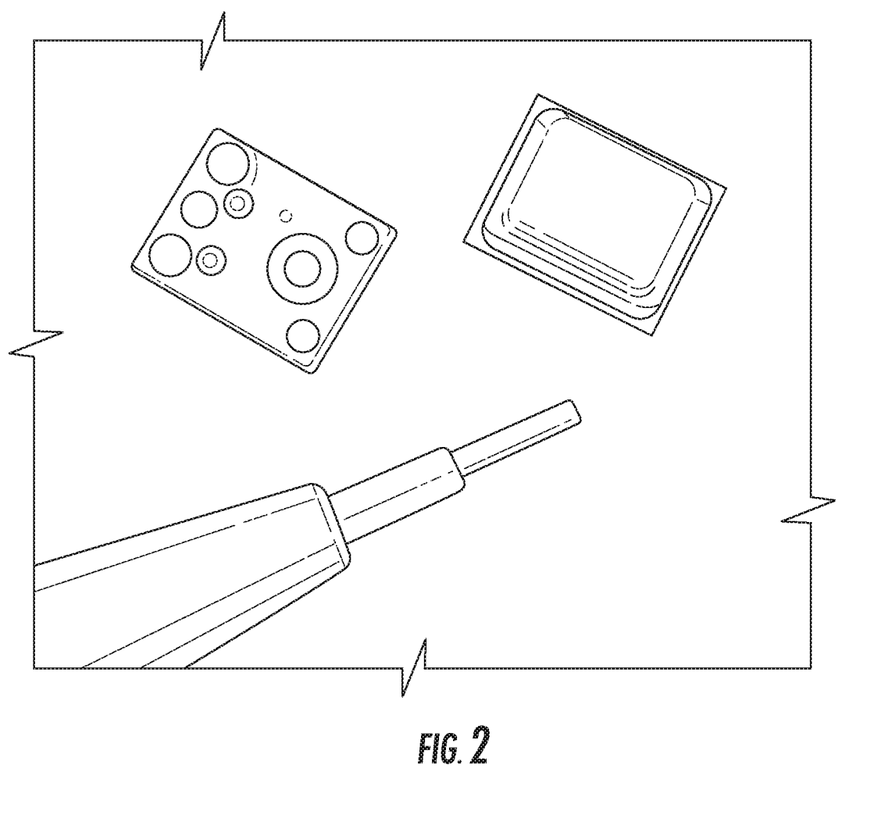
FIG. 2 is a representative example of an acoustic sensor shown with a mechanical pencil lead having a 0.5 mm diameter.

FIG. 2 shows an example of a commercially available capacitor-based acoustic sensor 10, shown with a mechanical pencil lead having a 0.5 mm diameter to illustrate its size. The size of certain acoustic sensors may be about 4 mm×3 mm×1 mm. Of course, the acoustic sensors may have other dimensions. Other types of acoustic sensors, such as piezoelectric-type micro acoustic sensors, may also be used. Thus, the type of acoustic sensor is not limited by this disclosure. However, in some embodiments, the acoustic sensor should be able to tolerate very low temperatures and immersion in a fluid.

Figure 3A:
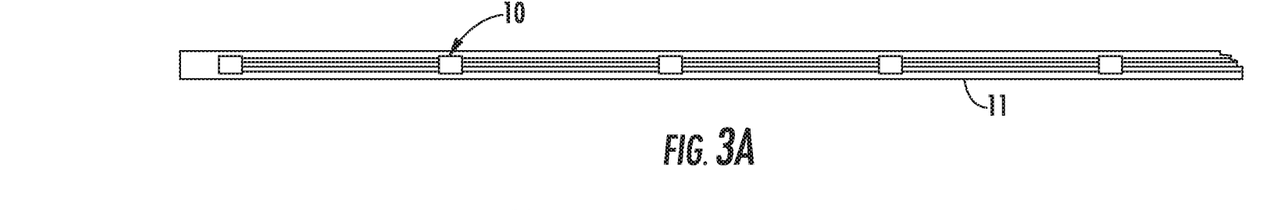
FIGS. 3A-3D shows various embodiments of an acoustic sensor array.
Figure 3B:
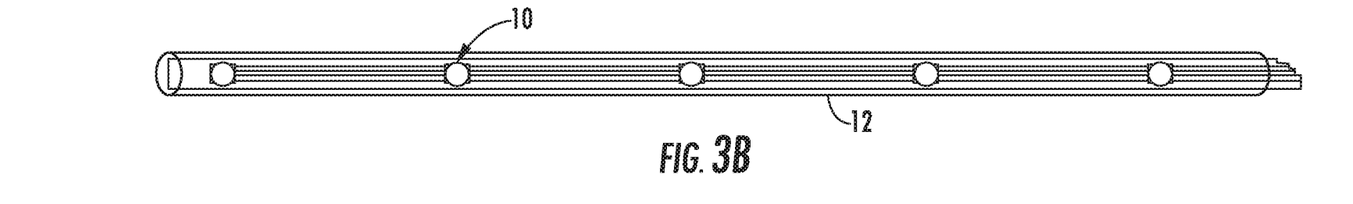
Figure 3C:
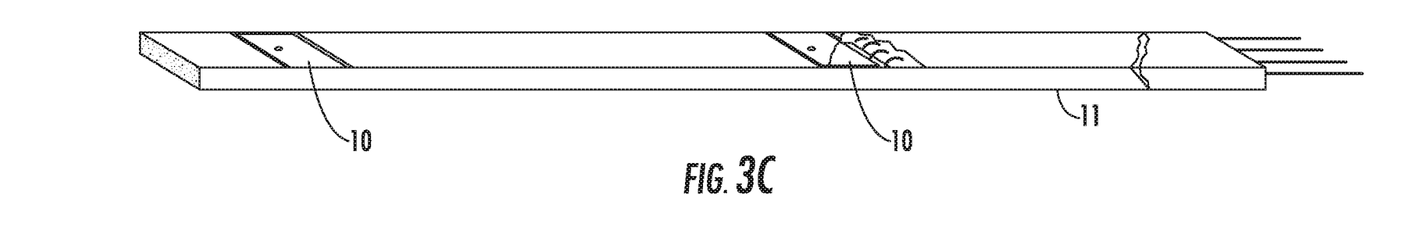
Figure 3D:
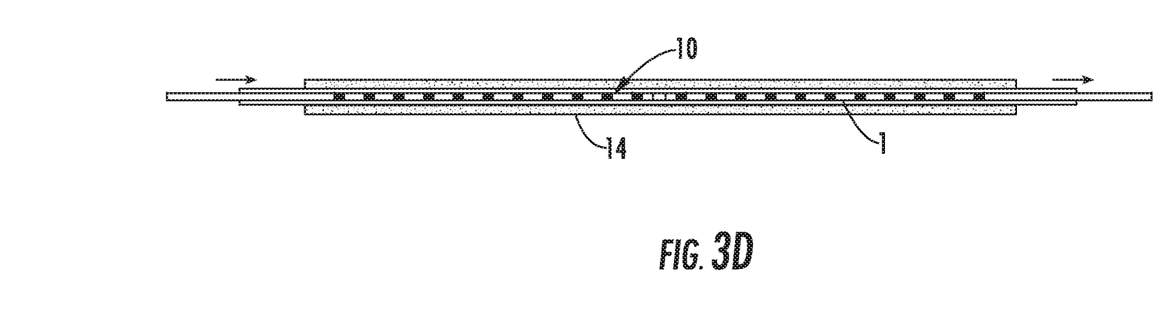

These acoustic sensors 10 may be mounted in a straight line on a narrow long flexible plate 11, as shown in FIG. 3A. The plate 11 may be constructed of any suitable material. The electrical connections between the acoustic sensors 10 may be embedded in the plate 11 or separate from the plate 11. FIG. 3C shows an enlarged illustration of the embodiment of FIG. 3A. In this embodiment, the electrical connections are embedded in the plate 11, however, other embodiments are possible. Only two acoustic sensors 10 are shown and the rightmost acoustic sensor 10 is partially exposed to show the details of the acoustic sensor 10. Alternatively, the acoustic sensors 10 may be mounted in a straight line in a long flexible porous tube 12, as shown in FIG. 3B. The porous tube 12 may be non-metal or metal. The acoustic sensors 10 may be mounted to minimize hydraulic resistance to reduce noises due to hydraulic flow turbulence. The acoustic sensor arrays 1 can be inserted from either end of a power transmission cable and/or a magnet conductor before or after magnet winding, as shown in FIG. 3D.

The acoustic sensors 10 of the present disclosure are intended to be operated in liquid and/or gas environments. In certain embodiments, the acoustic sensors may need to be robust in vacuum, since they might be exposed in vacuum. Consequently, in certain embodiments, the acoustic sensors 10 of the present disclosure may have different operational requirements from conventional commercial microphone type acoustic sensors. The sensor characteristics can be specific for each application to meet the required frequency responses.

As stated above and shown in FIG. 1A, the acoustic sensors 10 on the acoustic sensor array 1 are separated from each other by a separation distance Lx. The separation between adjacent acoustic sensors 10 does not need to be equal, however the location of each of the acoustic sensors 10 may preferably be known, in order to accurately identify the quench location from the sensor location.

The acoustic sensors 10 in an acoustic sensor array 1 may be electrically connected as shown in FIG. 3A. The power and ground supply lines of the acoustic sensors 10 may be connected in parallel, but the signal output of each acoustic sensor 10 may be connected independently to identify the sensor which generates an output signal. As shown in FIG. 3D, the acoustic sensor arrays 1 can be inserted from either end of a power transmission cable 14 and/or a magnet conductor before or after magnet winding. The arrows in FIG. 3D indicate the direction of coolant flow.

Figure 4A:
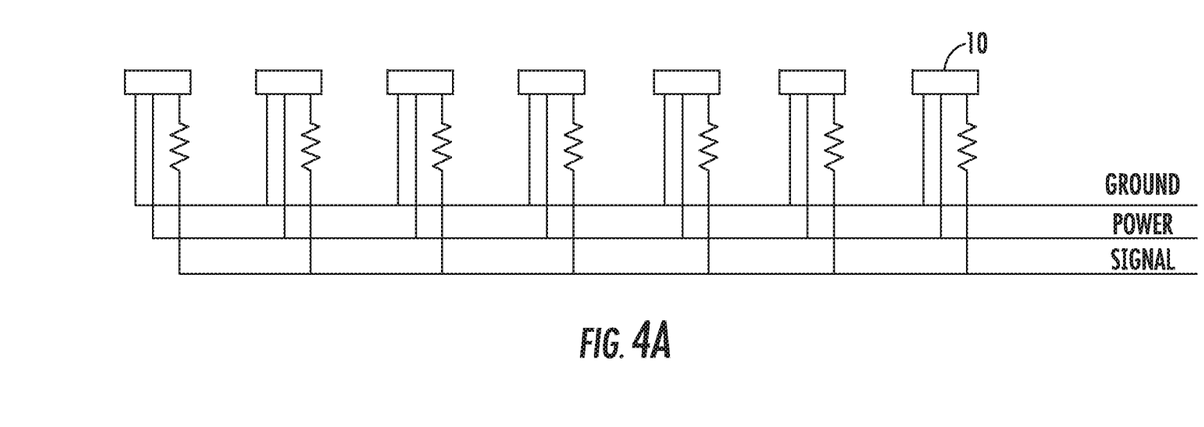
FIGS. 4A-4C show the electrical wiring of the acoustic sensor array according to three embodiments.

In certain embodiments, it may not be necessary to determine which acoustic sensor 10 outputs the signal. In such embodiments, the acoustic sensors 10 will not need to be independently wired. In other words, the sensor signal outputs of all of the acoustic sensors 10 can be connected in parallel as shown in FIG. 4A. In this embodiment, a single signal is created by the acoustic sensor array 1. This allows the system to be extremely flexible and easy to configure for any operational condition. This embodiment is beneficial when the detection of a quench or other abnormal event, but not its location, is desired.

Figure 4B:
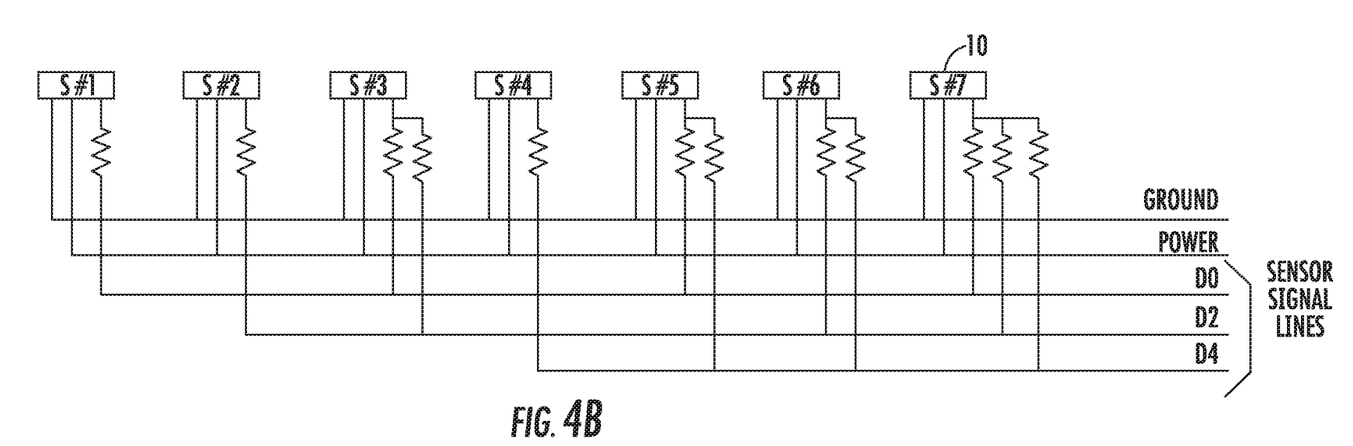

In certain embodiments, the number of wires can be reduced with a proper configuration. FIG. 4B illustrates, as an example, a five-wire method to connect seven acoustic sensors 10 (numbered S #1-S #7). The seven sensors 10 may be mounted on a flexible plate (such as the plate 11 in FIG. 3A) with ground and power wires and three sensor signal output wires, as shown in FIG. 4B. Each acoustic sensor 10 is powered with two lines: a ground wire and a power wire. The signal lines of D0, D2 and D4 are constructed with three wires in this case. The sensor wiring method in FIG. 4B can logically form a binary code. Using n wires, $2^n-1$ sensors can be connected (n=5 for 31 sensors), and the sensor can be identified by detecting which signal line numbers of the output signal are actuated. In FIG. 4B, the seven acoustic sensors 10 are connected to between one and three of the three wires: Sensor S #1 to D0, S #2 to D2, S #3 to D0 and D2, S #4 to D4, S #5 to D0 and D4, S #6 to D2 and D4, S #7 to D0, D2 and D4. When the output signals are actuated on D0 and D4 lines, the active acoustic sensor 10 generating the signal is known to be Sensor #5. The signal wires are connected to the acoustic sensors 10 through isolation resistors to prevent interference between the signal lines. It is noted that while seven acoustic sensors 10 with three signal wires are shown, this coding scheme may be used with any number of acoustic sensors 10 and signal wires. Further, while this describes a binary coding system, the output signals from the acoustic sensors 10 may be configured in another manner, if desired.

Figure 4C:
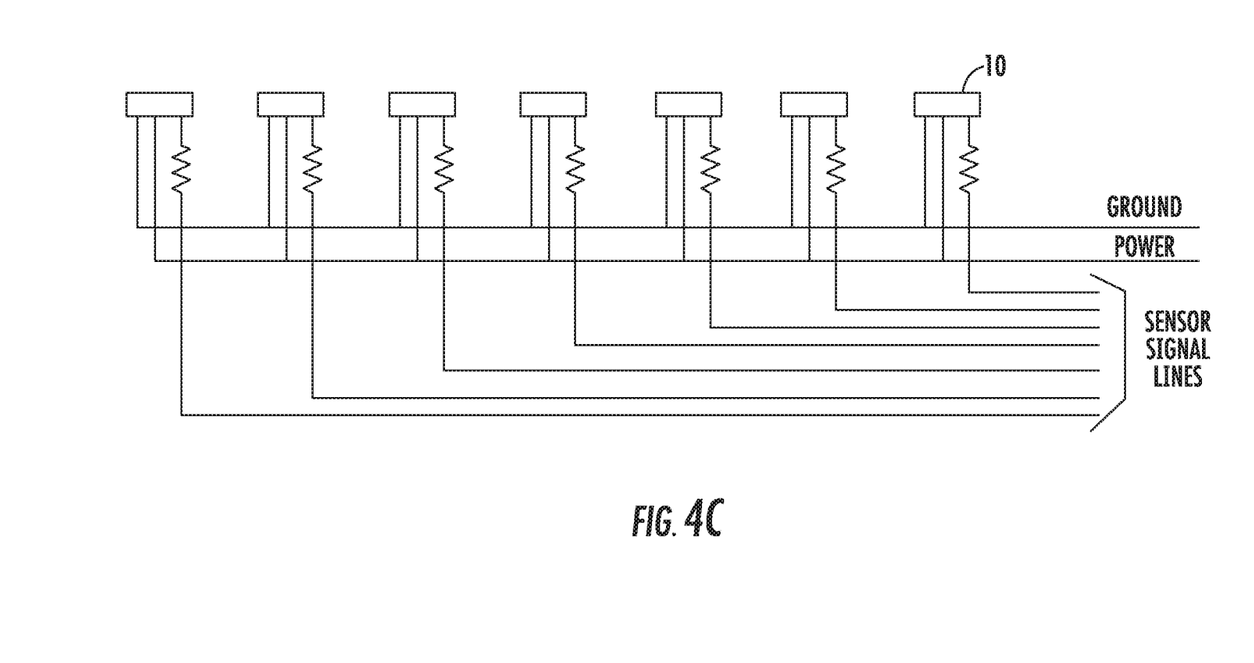

In another embodiment, the output of each acoustic sensor 10 is separate from each other output, as shown in FIG. 4C. In other words, if there are N acoustic sensors 10, there are N output signals.

In another method to reduce the number of electric wires, well-known fiber-optic communication methods can be used. Electric signals of acoustic sensors are converted into optical signals by the use of electro-optical transducers, and the optical signals are transmitted through the optical fibers. The optical signals received are converted into electric signals. Multiple acoustic sensor signals can be read using an optical technology with optical fibers.

In order to detect responses from the acoustic sensors 10 from the coolant of a superconducting conductor, the acoustic sensor array 1 may be inserted in a coolant channel in a superconducting magnet conductor and/or power transmission cable.

Figure 5A:
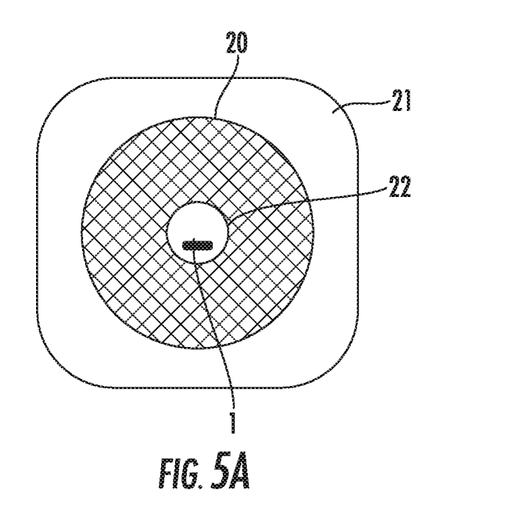
FIGS. 5A-5C show the acoustic sensor array in various configurations.
Figure 5B:
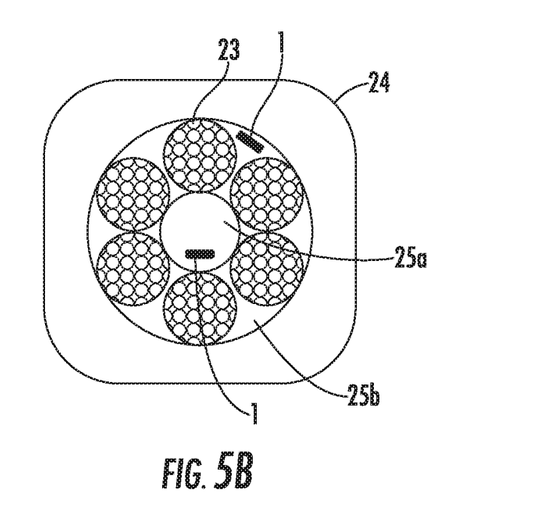
Figure 5C:
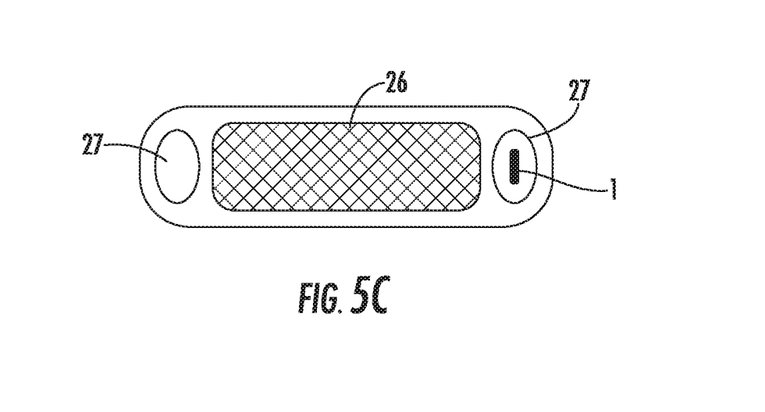

For a Cable in Conduit Conductor (CICC), the acoustic sensors 10 can be inserted in the coolant channel, as shown in FIGS. 5A-5C. These figures show the cross-sections of three types of different conventional CICC superconducting cables. FIG. 5A shows a bundled single cable 20 in a square conduit 21 with a center coolant channel 22. FIG. 5B shows a multiple cabled conductor of six sub-cables 23 in a square conduit 24 with a center coolant channel 25a and six corner coolant channels 25b. FIG. 5C shows a rectangular conductor with two coolant channels 27. In each embodiment, the superconducting cable commonly comprises many fine wires of about 1 mm to 10 mm width and 0.1 mm thickness tapes or about 1 mm diameter or less. The acoustic sensor array 1 is shown in each conductor in FIGS. 5A-5C. The acoustic sensor array 1 may be inserted in any coolant channel. In the case of FIG. 5B, the acoustic sensor array 1 can be inserted in center coolant channel 25a, one of the corner coolant channels 25b, or both. In the case shown in FIG. 5C, the acoustic sensor array 1 can be inserted in one of the coolant channels 27. In other embodiments, an acoustic sensor array 1 may be inserted in both coolant channels 27.

In general, the acoustic wave propagation speed in liquid coolant, such as helium and hydrogen, is about 1400 m/s. Therefore, if the separation of the acoustic sensors 10 in the acoustic sensor array 1 is Lx=10 m, the acoustic wave signal of a superconductor will be detected in less than 3.6 ms. This is determined by half the separation, divided by the speed of propagation, or 5 m/1400 m/s. If the separation of the acoustic sensors 10 is Lx=2 m, the acoustic signal can be detected in about 0.8 ms in liquid coolant. The detection delay time due to the sensor location can be reduced by reducing the sensor separation distance Lx.

Thus, the present disclosure of an acoustic sensor array for use with a superconducting conductor or a superconducting magnet allows spatially continuous monitoring along a superconducting conductor or a magnetic conductor with a good spatial resolution by reducing the sensor separation Lx. In a case of gas coolant, such as helium or hydrogen gas, the acoustic wave propagation speed is slower than that in liquid. Thus, the separation Lx may be reduced to achieve acceptable detection times.

To improve the detection signal quality of an acoustic wave using an acoustic sensor 10, electronic filtering and frequency characteristic adjustment of the acoustic sensor 10 can be used. In one embodiment, narrow band-pass filtering of the electronic signal may be used to enhance the detection sensitivity in order to detect only desired signals. In another embodiment, the analog signal can be digitized at the sensor site to improve the system Signal-to-Noise Ratio (SNR). Digital acoustic sensors can be used instead of the analog type of acoustic sensors for this purpose. In another embodiment, the signal quality can also be improved by employing software to reduce noise. In certain embodiments, signal improvement, such as background noise cancellation and acoustic echo signal reduction, can be performed by using signal conditioning and Doppler effect technologies, in order to detect effectively an abnormal location, such as a quench, of a superconducting conductor.

Conventional acoustic sensors for voice microphone applications require a flat frequency response between about 100 Hz and 10 kHz. However, the frequency response for the present applications can be narrower. The frequency range of the acoustic sensor 10 sensor may be matched to the frequency range of the specific applications corresponding to an event to be detected.

Furthermore, acoustic sensors 10 may be used in a high magnetic field, in an environment with high pressure (gas or liquid) and low temperature for certain applications, such as CICC superconducting magnet applications. Certain applications require the sensor to be in vacuum before adding the coolant in order to clean the inside of the conduit enclosure. For such applications, specially developed acoustic sensors may be used.

Figure 6:
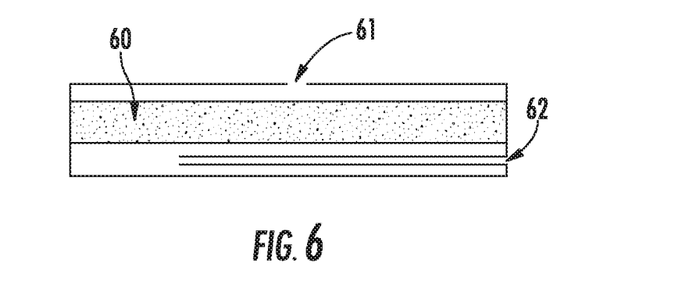
FIG. 6 is a cross-section of an acoustic sensor for a transient acoustic wave in a high-pressure environment.

In one embodiment, a high-pressure application may employ an acoustic sensor 60 having two sensing sides with differential acoustic paths as shown in FIG. 6. In this example, there are two acoustic paths 61, 62. Acoustic path 62 has, for example, a narrow long channel to produce a response to an acoustic wave that may be delayed. In contrast, the acoustic path 61 is much shorter and therefore responds more quickly to an acoustic signal. Thus, the transient response of the acoustic sensor 60 first affects the acoustic path 61, since acoustic path 61 is shorter than acoustic path 62. Therefore, the acoustic sensor 60 can detect a quick temporary sound wave. For a steady state of high pressure or low pressure in vacuum, both acoustic paths 61, 62 produce the same pressure to the acoustic sensor 60. They are balanced and therefore produce no output signal. That is, the acoustic paths 61, 62 have different time responses, and therefore only a fast time dependent phenomena of a quick acoustic signal in a high-pressure environment such as a quench of a superconducting magnet in a high-pressure coolant can be detected. This type of acoustic sensor 60 may be also used in vacuum. For cryogenic applications, the acoustic sensor 60 may be made of materials for low temperature use. For magnetic field applications, the acoustic sensors 60 may be made of non-magnetic materials without strongly magnetic materials such as iron, nickel, non-magnetic stain-less steel, etc.

Figure 7:
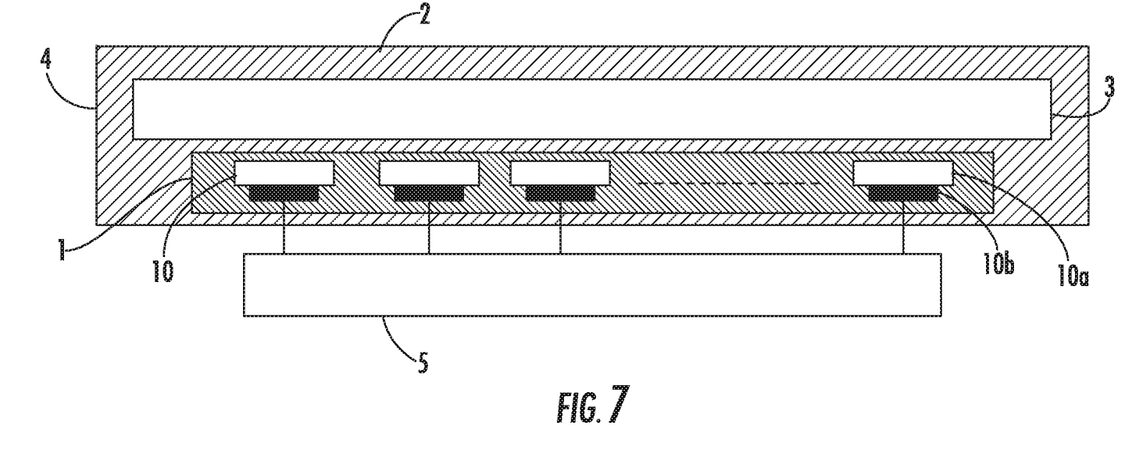
FIG. 7 shows a system for detecting thermal events using an acoustic sensor array.

FIG. 7 shows a representative system that employs the acoustic sensor array 1 described herein to detect acoustic waves due to abnormal events, such as changes in temperature that result in vaporization of the coolant 2. An acoustic sensor array 1 is disposed in a coolant 2 spaced apart from the superconducting element 3. The acoustic sensor array 1 may have any suitable number of acoustic sensors 10. For example, in certain embodiments, there may be as few as one acoustic sensor 10. The acoustic sensor 10 may be comprised of an acoustic sensing element 10a, such as an electric capacitor and piezo element, and an electric transducer 10b, such as a voltage amplifier and an electric-to-optical coupling convertor. The coolant 2 may be a liquid or gas, such as helium, hydrogen, nitrogen, or others. A superconducting element 3, such as a conductor or magnet, is also disposed in the coolant 2. The coolant 2, acoustic sensor array 1, and superconducting element 3 are all disposed in an enclosure 4. In certain embodiments, the enclosure may be one of the enclosures shown in FIGS. 5A-5C. Wires from the acoustic sensor array 1 may exit the enclosure 4 and attach to a controller 5. The controller 5 can be implemented in numerous ways, such as with dedicated hardware, or with general purpose hardware, such as a computer system, that is programmed using microcode or software to perform the functions recited herein. The controller 5 may comprise a processing unit and a local memory device. The local memory device may contain instructions, which, when executed by the processing unit, enable the system to perform the functions described herein. This local memory device may be a non-volatile memory, such as a FLASH ROM, an electrically erasable ROM or other suitable devices. In other embodiments, the local memory device may be a volatile memory, such as a RAM or DRAM. Additionally, the controller 5 may include a user input device, such as a keyboard, mouse, touch screen or another suitable device. The system may also include a display device, such as a computer screen, LED display, touch screen or the like. The user input device and the display device are all in communication with the processing unit.

The controller 5 receives the signals from the acoustic sensor array 1. While FIG. 7 shows each acoustic sensor 10 having a dedicated signal wire in communication with the controller 5, the configuration of the signal wires may be as described in any of FIGS. 4A-4C. The controller 5 may detect whether any signal wire is actuated. The controller 5 may further determine which signal wire or wires are actuated in order to determine the location of the abnormal event. The controller evaluates the signals of each sensors and times of the signal received. From this information, the event location can be determined. The controller 5 may sample the signal wires at regular intervals, such as every millisecond. Of course, other sampling rates may also be used. In another embodiments, the signals wires may be treated as an interrupt, where any actuation of a signal wire causes the controller 5 to execute an interrupt routine to determine the location of the abnormal event.

In certain embodiments, two or more acoustic sensors 10 of the acoustic sensor array 1 may detect the same event. Several different techniques may be used to detect the location of the event. In one embodiment, the controller 5 determines the first acoustic sensor which initially detects the event. The controller 5 then identifies the event as being near that first acoustic sensor. In another embodiment, the controller 5 determines the time that each acoustic sensor 10 detected the event. It then uses the time that each acoustic sensor 10 detected the event as well as the location of each acoustic sensor 10 to more accurately pinpoint the location of the event. For example, assume that a first acoustic sensor detects the event and a second acoustic sensor detects the event 0.5 msec later. Also assume that Lx is 10 meters and the propagation rate in the coolant is 1400 m/s. From this information, it can be determined that the second acoustic sensor is 0.7 m further from the event than the first acoustic sensor (0.5 msec*1400 m/s). If Lx is 10 m, then it can be determined that the event occurs 4.65 meters from the first acoustic sensor and 5.35 meters from the second acoustic sensor. In yet another embodiment, the controller may use the amplitude of each signal wire to help pinpoint the location of the event. In other embodiments, the controller 5 may use both time information and amplitude information to pinpoint the location of the event.

A test was performed to verify the effectiveness of the present system. An acoustic sensor, such as that shown in FIG. 2, was disposed in a container filled with water. The output of the acoustic sensor was attached to an amplifier to increase the amplitude of its output. The output of the amplifier was then input to a voltmeter and an oscilloscope. A syringe was used to inject air bubbles into the water. These air bubbles are intended to simulate a quench condition. The presence of bubbles was detected by the acoustic sensor and was visible both on the oscilloscope and the voltmeter. This demonstrated that the present acoustic sensor method to able to detect a quench like event in a liquid coolant, namely water.

Further, it is also possible to utilize the acoustic sensor array 1 of the present disclosure in environments that do not employ a coolant fluid. For example, in certain embodiments, the acoustic sensor array 1 may be disposed in a vacuum. In this embodiment, the acoustic sensors 10 may be mounted directly on the superconducting element.

For example, the acoustic sensors 10 or the acoustic sensor array 1 may be mounted on the surface of the superconductor or the wall of the magnet winding for a bath-cooling condition of a bath cooled device or magnet. In other words, the acoustic sensor array 1 can be also used for a cryocooled dry superconducting magnet system that do not employ a coolant fluid. The acoustic sensor array 1 described herein can detect a sound wave due to an abnormal event through transmission of the acoustic wave through the magnet body. The use of an acoustic sensor array made up of multiple sensors makes it possible to pinpoint the location of an abnormal event.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A system for detecting events in a superconducting system, comprising:
    an enclosure;
    a coolant fluid disposed in the enclosure;
    a superconducting element disposed within the enclosure;
    the coolant fluid in a coolant channel disposed in the superconducting element; and
    an acoustic sensor array disposed in the coolant channel, wherein the acoustic sensor array detects an event in the superconducting element based on detecting acoustic waves generated due to a temperature change by the event and transmitted in the coolant fluid.

2. The system of claim 1, wherein the coolant fluid comprises a liquid.

3. The system of claim 1, wherein the coolant fluid comprises a gas.

4. The system of claim 1, wherein the superconducting element comprises a superconducting conductor.

5. The system of claim 1, wherein the superconducting element comprises a superconducting magnet.

6. A system for determining a location of a thermal event in a superconducting system, comprising:
    an enclosure;
    a coolant fluid disposed in the enclosure;
    a superconducting element disposed within the coolant fluid; and an acoustic sensor array disposed in the coolant fluid, the acoustic sensor array comprising a plurality of acoustic sensors, wherein one or more of the plurality of acoustic sensors in the acoustic sensor array detects the thermal event in the superconducting element based on detecting acoustic waves generated due to a temperature change by the thermal event and transmitted in the coolant fluid, and a location of the thermal event is determined based on which one of the plurality of acoustic sensors first detects the acoustic waves.

7. The system of claim 6, wherein the acoustic sensor array comprises a linear array of equally spaced acoustic sensors.

8. The system of claim 6, further comprising a controller, wherein outputs of the acoustic sensor array are in communication with the controller.

9. The system of claim 8, wherein each of the plurality of acoustic sensors has an optical fiber cable in communication with the controller.

10. The system of claim 8, wherein each of the plurality of acoustic sensors has an independent output.

11. The system of claim 8, wherein the outputs of the plurality of acoustic sensors are combined into a smaller number of wires, wherein a combination of wires are actuated if an event is detected and the combination of wires that is actuated is indicative of the acoustic sensor that detected the event first.

12. The system of claim 6, wherein the superconducting element comprises a bundled cable with a center coolant channel, wherein the acoustic sensor array is disposed in the center coolant channel.

13. The system of claim 6, wherein the superconducting element comprises a multiple cabled conductor of sub-cables with a center coolant channel, wherein the acoustic sensor array is disposed in the center coolant channel.

14. The system of claim 6, wherein the superconducting element comprises a rectangular conductor with coolant channels disposed on either side of the superconducting element, and wherein the acoustic sensor array is disposed in one of the coolant channels.

15. A method of detecting a location of an abnormal event of a superconducting element disposed in a coolant fluid, comprising:
disposing an acoustic sensor array in the fluid, proximate to the element, the acoustic sensor array comprising a plurality of acoustic sensors;
detecting an acoustic wave, caused by a temperature change due to the abnormal event in the superconducting element that is transmitted through the coolant fluid, by at least one acoustic sensor in the acoustic sensor array;
determining the location of the abnormal event based on an identity and location of the at least one acoustic sensor that detects the acoustic wave and a time that the at least one acoustic sensor detects the acoustic wave.

16. The method of claim 15, wherein the coolant fluid comprises a liquid.

17. The method of claim 15, wherein the plurality of acoustic sensors are spaced at regular intervals.

18. The method of claim 15, wherein the coolant fluid comprises a gas.

19. A system for determining a location of a thermal event in a superconducting system, comprising:
an enclosure;
a coolant fluid disposed in the enclosure;
a superconducting element disposed within the coolant fluid; and
an acoustic sensor array disposed in the coolant fluid, the acoustic sensor array comprising a plurality of acoustic sensors, wherein at least one acoustic sensor in the acoustic sensor array detects the thermal event in the superconducting element based on detecting acoustic waves generated due to a temperature change by the thermal event and transmitted in the coolant fluid, and a location of the thermal event is determined based on an identity and location of the at least one acoustic sensor that detects the acoustic wave and a time that the at least one acoustic sensor detects the acoustic wave.

20. The system of claim 19, wherein the acoustic sensor array comprises a linear array of equally spaced acoustic sensors.

21. The system of claim 19, further comprising a controller, wherein outputs of the acoustic sensor array are in communication with the controller.

22. The system of claim 21, wherein each of the plurality of acoustic sensors has an optical fiber cable in communication with the controller.

23. The system of claim 21, wherein each of the plurality of acoustic sensors has an independent output.

24. The system of claim 19, wherein the superconducting element comprises a bundled cable with a center coolant channel, wherein the acoustic sensor array is disposed in the center coolant channel.

25. The system of claim 19, wherein the superconducting element comprises a multiple cabled conductor of sub-cables with a center coolant channel, wherein the acoustic sensor array is disposed in the center coolant channel.

26. The system of claim 19, wherein the superconducting element comprises a rectangular conductor with coolant channels disposed on either side of the superconducting element, and wherein the acoustic sensor array is disposed in one of the coolant channels.

* * * * *